United States Patent [19]

Sabourin et al.

[11] 4,128,588

[45] Dec. 5, 1978

[54] PROCESS FOR THE PREPARATION OF NITROPHENYL HYDROXY SUBSTITUTED ACETYLENE AND CONVERSION TO NITROPHENYLACETYLENE

[75] Inventors: Edward T. Sabourin, Allison Park; Charles M. Selwitz, Monroeville, both of Pa.

[73] Assignee: Gulf Research & Development Company, Pittsburgh, Pa.

[21] Appl. No.: 840,553

[22] Filed: Oct. 11, 1977

[51] Int. Cl.$^2$ .................... C07C 79/10; C07C 33/04
[52] U.S. Cl. .................................... 260/645; 568/705
[58] Field of Search ........................... 260/618 E, 645

[56] References Cited

U.S. PATENT DOCUMENTS 4,016,214  4/1977  Douglas et al. ............... 260/645 X Primary Examiner—Leland A. Sebastian

[57] ABSTRACT

Nitrophenyl hydroxy substituted acetylene, which can be converted to nitrophenylacetylene is prepared by reacting a nitrobromobenzene with a substituted terminal acetylene compound containing at least three carbon atoms and a hydroxy group on the carbon atom adjacent to the acetylene group in the presence of a dialkyl or trialkyl amine solvent and a catalyst system consisting of a palladium complex containing two halogen moities and two tri-substituted phosphine moieties. A cuprous iodide promoter is also employed in the reaction sequence.

10 Claims, No Drawings

PROCESS FOR THE PREPARATION OF NITROPHENYL HYDROXY SUBSTITUTED ACETYLENE AND CONVERSION TO NITROPHENYLACETYLENE

This invention relates to a process for producing nitrophenyl hydroxy substituted acetylenes and in particular for producing 2-methyl-4(3-nitrophenyl)3-butyn-2-ol.

BACKGROUND OF THE INVENTION

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetylene-terminated polyimides which are described, for example, in U.S. Pat. No. 3,845,018 and U.S. Pat. No. 3,879,349, both to Norman Bilow et al., is the preparation of the monomers which include in one instance the preparation of meta-aminophenylacetylene (APA). The process of this invention relates to improved procedures for the preparation of precursors to nitrophenylacetylene, which itself is a precursor to APA.

DESCRIPTION OF THE PRIOR ART

The description of the preparation of APA contained in the teachings of Bilow et al. in U.S. Pat. No. 3,845,018 involves a large number of expensive and time-consuming steps. Thus Bilow et al. in Column 4, lines 41 et seq., teach that an aromatic compound having both nitro and acetyl substituents is reacted, preferably under reflux, with dimethylformamide and phosphorus oxychloride to convert the acetyl radical to —C(Cl)=CHCHO. The reaction is exothermic, and external cooling is needed to keep it at approximately room temperature. The β-chloro-substituted aldehyde radical is converted to —C≡CH by refluxing a solution of the compound in dioxane and sodium hydroxide. The product is extracted with an organic solvent such as ether; the organic solution is dried; the solvent is removed; and the product recovered by vacuum distillation.

Improved techniques over those taught by Bilow et al. obviously have to be developed in order to improve the competitive position of the resultant acetylene-terminated polyimides in the marketplace.

The compound of chief interest for this invention is meta-nitrophenylacetylene. An article entitled, "A Convenient Synthesis of Acetylenes: Catalytic Substitution of Acetylenic Hydrogen with Bromoalkenes, Iodoarenes, and Bromopyridines" by Kenkichi Sonogashira et al., published in Tetrahedron Letters, No. 50, pages 4467–4470, 1975 (Pergamon Press, Gr. Brit.), suggests that iodobenzene could be reacted with acetylene in the presence of a complex catalyst system to produce phenylacetylene. There is no suggestion in the article that bromobenzene or other bromoarenes could be utilized, but only that bromoalkenes or bromopyridines could be substituted for the iodoarene compounds. An attempt was made to react meta-nitrobromobenzene with acetylene using the same catalyst under the same conditions and using the same solvent as taught by Sonogashira et al., but no reaction was observed after 6 hours, the six hours being the same time period as used by Sonogashira et al. for the reaction of acetylene with iodobenzene. Sonogashira et al. also present working examples using other acetylenic reactants besides acetylene, namely, certain substituted terminal acetylenes, including 2-propyn-1-ol (HC≡C—CH$_2$—OH) and phenylacetylene. An attempt was then made to react bromobenzene with an analog of 2-propyn-1-ol, i.e. 2-methyl-3-butyn-2-ol using the same conditions as taught by Sonogashira et al., except the temperature was increased from room temperature to 56° C.; and it was found, as will be shown more fully below, that the reaction was extremely sluggish, despite the higher temperature, so that the result was of substantially no interest from a commercial viewpoint.

Earlier work has been done in Russia relating to acetylenic condensation and is contained in an article entitled, "Acetylenic Condensation in the Series of Substituted Iodobenzenes", by M. S. Shvartsberg et al. (Izvestiya Akademii Nauk SSSR, Seriya Khimicheskaya, No. 6, pages 1306–1310, June 1971). The Russian work indicates that nitroiodobenzene can be reacted with rather complex substituted acetylenes in the presence of a potassium carbonate copper catalyst system to produce nitrophenyl substituted acetylenes, which can be hydrolyzed to form less complex substituted nitrophenylacetylenes, which can be further reacted with a weak base to form nitrophenylacetylene. There is no indication or teaching in the Russian article that the bromo analog of the iodonitrobenzene can be employed using the peculiar base catalyst of the Russians. It would thus appear from the prior art that iodobenzene (Sonogashira et al.) or nitroiodobenzene (Shvartsberg et al.) will work in different catalyst systems with various types of acetylenic or substituted acetylenic charge stocks in such a manner that the acetylenic charge stock substitutes for the iodo group on the benzene nucleus. None of the prior art, however, dictates that bromoarenes can be employed in either of the catalyst systems of the prior art.

Surprisingly, however, and in accordance with the invention, it has been found that nitrophenyl hydroxy substituted acetylenes can be prepared from nitrobromobenzene by the reaction of the nitrobromobenzene with a substituted terminal acetylene compound containing at least 3 carbon atoms and a hydroxy group on the carbon atom adjacent to the acetylene group at mild conditions to produce a substantial yield of a nitrophenyl hydroxy substituted acetylene. The reaction occurs in the presence of an amine-type solvent, which serves not only as a solvent but as a complexing agent with the byproduct HBr, which is produced during the reaction. The substitution reaction is catalyzed by a complex palladium salt containing two halogen moieties and two substituted phosphine moieties where the substituents on the phosphorus are phenyl, lower alkyl groups and substituted phenyl groups. The catalytic activity of the palladium complex salt is promoted with a small amount of cuprous iodide.

Any nitrobromobenzene can suitably be employed in the process of this invention. The source of the nitrobromobenzene or its method of preparation are well known in the art and are not critical to the operation of the process of this invention. The suitable nitrobromobenzenes are, of course, the ortho-, meta- and para-nitrobromobenzenes; and of these, meta-nitrobromobenzene is preferred.

The nitrobromobenzene is reacted with a substituted terminal acetylene compound containing at least 3 carbon atoms and a hydroxy group on the carbon atom adjacent to the acetylene group. The preferred substituted terminal acetylene compounds are those having the formula:

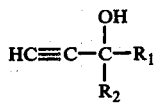

where $R_1$ and $R_2$ can be the same or different and are selected from the group consisting of hydrogen, lower alkyl groups having from 1 to 4 atoms, phenyl, substituted phenyl; or where $R_1$ and $R_2$ can form a saturated 5- or 6-membered ring. The preparation of these compounds is well known in the art and forms no part of the subject invention. For example, acetylene can be reacted with acetone to form 2-methyl-3-butyn-2-ol, which is the preferred substituted terminated acetylenic charge stock for use in the process of this invention. Other suitable acetylenic compounds include the following:
 3-methyl-1-pentyn-3-ol;
 3-ethyl-1-pentyn-3-ol;
 2-phenyl-3-butyn-2-ol;
 1-ethynylcyclohexanol; and
 1-ethynolcyclopentanol.

Usually the nitrobromobenzene is reacted with the terminal acetylene compounds in a molar ratio of about 1:1, but suitable molar ratios include those from 1:0.5 to 1:100 and are more preferably from 1:1 to 1:5.

The reaction of the nitrobromobenzene with the terminal acetylenic compounds defined above occurs in the presence of a dialkyl or trialkyl amine solvent and a complex catalyst system. The amine solvent can suitably have the formula:

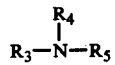

where $R_3$, $R_4$ and $R_5$ can be the same or different and are selected from the group consisting of hydrogen and lower alkyl groups having from 1 to 4 carbon atoms, with the proviso that no more than one of said R groups can be hydrogen. Suitable solvents include but are not limited to dimethylamine, trimethylamine, diethylamine, triethylamine, ethylpropylamine, ethylbutylamine and dibutylamine.

The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from 1 to 4 carbon atoms, and substituted phenyl groups. A suitable palladium complex would have the formula:

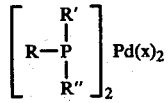

where x is bromine, iodine or chlorine, and R, R' and R" are the same or different and are selected from the group consisting of phenyl, alkyl groups having from 1 to 4 carbon atoms and substituted phenyl groups. The substituents on the phenyl groups can include alkyl groups having from 1 to 4 carbon atoms, alkoxy groups having 1 to 4 carbon atoms, and halogen. A suitable list of representative palladium complex salts which can be employed in the process of this invention include:
 bis(triphenylphosphine)palladium dibromide;
 bis(tri-n-butylphosphine)palladium dichloride;
 bis(tri-t-butyl-phosphine)palladium dichloride;
 bis(tri-i-butylphosphine)palladium dichloride;
 bis(triethylphosphine)palladium dichloride;
 bis(tripropylphosphine)palladium dichloride;
 bis(tritolylphosphine)palladium dichloride;
 bis(trianisylphosphine)palladium dichloride;
 bis(tri(chlorophenyl)phosphine)palladium dichloride; and
 bis(tri(bromophenyl)phosphine)palladium dichloride.

A promoter for the catalyst system is also employed, and this promoter comprises cuprous iodide. Usually the amount of the promoter is very small, and suitable amounts of promoter inlcude a molar ratio of promoter to palladium catalyst of from 0.5:1 to 20:1, preferably from 1:1 to 5:1. The amount of the palladium catalyst employed in the reaction is usually from 0.01 to 1.0 mole percent based on nitrobromobenzene and is more preferably from 0.02 to 0.05 mole percent based on nitrobromobenzene.

The reaction of the nitrobromobenzene with the acetylene-terminated compound is really a substitution-type reaction, and the reaction conditions to employ are relatively mild and include a temperature from about 20° to 200° C. and more preferably from 50° to 125° C. However, it is considered that the reaction conditions are not critical, and the precise reaction conditions to employ would be obvious to one having ordinary skill in the art. The reaction conditions should be such that the solvent chosen is maintained in the liquid phase. The normal reaction pressure is atmospheric; however, increased reaction pressures of up to 250 psig (1.7 MPa) or higher can be employed. The reaction time to employ is somewhat dependent on the particular charge stock and catalyst chosen and, of course, on the reaction temperature. Usually the reaction time is from 1 hour to 150 hours, but is more usually from 3 hours to 24 hours. Higher or lower reaction times can be employed, for timing is not a critical parameter but rather in many cases serves to increase the yield of the desired reaction product.

A typical reaction sequence is shown in Equation 1 below, which utilizes certain specific charge stocks which fall within the scope of the charge stocks defined above.

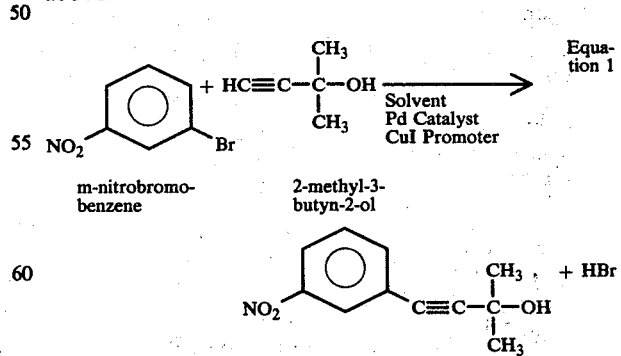

Referring to Equation 1 above, it can be seen that a byproduct of the reaction sequence is HBr. The HBr cannot be permitted to remain in the reaction product because of its corrosive nature.

It is one of the purposes of the amine solvent to react with the HBr in order to produce the amine hydrobromide salt and render it inactive. The amount of the amine solvent to employ in the reaction is not critical but must thus be sufficient to maintain the reactants in the liquid phase plus provide sufficient amine to react with the byproduct HBr. Amounts of solvent from 500 to 700 ml per mole of nitrobromobenzene have successfully been employed. However, greater or lesser amounts can be employed, and the particular amount to employ would be within the normal skill in the art given the criteria set forth above.

The invention will be further described with reference to the following experimental work.

In all of the experiments to follow, a three-necked flask equipped with a magnetic stirrer, thermometer, condenser, nitrogen inlet and outlet, a rubber septum sample port and a heating mantle was employed. The

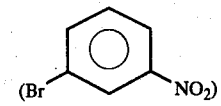

(Br—⟨⟩—NO₂)

was reacted under a nitrogen atmosphere with 2-methyl-3-butyn-2-ol

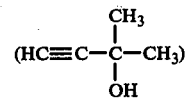

$$(HC{\equiv}C-\underset{\underset{OH}{|}}{\overset{\overset{CH_3}{|}}{C}}-CH_3)$$

using $[(C_6H_5)_3P]_2PdCl_2$ as the catalyst; CuI as the promoter; and various amines as solvents at varying reaction conditions. The runs are summarized in Table 1 below:

TABLE 1
REACTION OF 1-BROMO-3-NITROBENZENE WITH 2-METHYL-3-BUTYN-2-OL AT ATMOSPHERIC PRESSURE

| Ex. No. | Feed Stock Halide mmol | Feed Stock Alkyne mmol | Catalyst & Promoter [(C₆H₅)₃P]₂PdCl₂ mmol | Catalyst & Promoter CuI mmol | Solvent | Ml | Reaction Conditions Temp. °C. | Reaction Time in Hrs. to 50% Conv. | Reaction Time in Hrs. Total | Based on Bromonitrobenzene % Conv. | Based on Bromonitrobenzene % Eff. | Based on Bromonitrobenzene % Yield. |
|---|---|---|---|---|---|---|---|---|---|---|---|---|
| 1 | 10 | 10 | 0.07 | 0.05 | Diethylamine | 60 | ambient | 2 | 21 | 98 | — | — |
| 2 | 100 | 100 | 0.07 | 0.05 | Diethylamine | 200 | ambient | 34 | 118 | 86 | 94 | 81 |
| 3 | 100 | 100 | 0.07 | 0.05 | Diethylamine | 200 | 56 | 11 | 46 | 96 | 88 | 84 |
| 4 | 100 | 100 | 0.07 | 0.50 | Diethylamine | 200 | 56 | 1 | 45 | 89 | 96 | 85 |
| 5 | 100 | 100 | 0.07 | 0.25 | Diisopropylamine | 200 | 100 | 0.5 | 19 | 98 | a | a |
| 6 | 100 | 140 | 0.07 | 0.25 | Triethylamine | 200 | 90 | 0.2 | 16 | ~100 | a | a |
| 7 | 100 | 120 | 0.07 | 0.25 | Pyridine | 200 | 110 | — | 4 | 0 | — | — |
| 8 | 300 | 450 | 0.07 | 0.25 | Triethylamine | 200 | 90 | 0.5 | 21 | 95 | a | a |
| 9 | 100 | 140 | 0.07 | 0.25 | Triethylamine | 200 | 90 | 0.2 | 3 | ~100 | a | a |
| 10[b] | 100 | 140 | — | — | — | — | 90 | 1 | 22 | ~85 | a | a |
| 11[c] | — | — | — | — | — | — | 90 | — | 3 | 0 | a | a |
| 12[d] | 100 | 140 | 0.07 | — | — | — | 90 | 0.5 | 21 | ~90 | a | a |
| 13 | 10 | e | 0.07 | 0.05 | Diethylamine | 60 | ambient | — | 6 | 0 | 0 | 0 |
| 14 | 10[f] | 10[f] | 0.07 | 0.25 | Diethylamine | 60 | 56 | — | 116 | 13 | — | —. |
| 15 | 10[g] | 10 | 0.07 | 0.05 | Diethylamine | 60 | ambient | — | 19 | trace | — | — |

[a]Not worked up individually; combined for preparation of material for subsequent steps. A combined yield of 83% distilled product was obtained (88% efficiency).
[b]The product from Ex. 9 was filtered under an N₂ blanket to remove the bromide salt (EtN · HBr) which inhibits stirring, and a fresh charge of reactants was added.
[c]The product from Ex. 10 was filtered under an N₂ blanket to remove the bromide salt (EtN · HBr) which inhibits stirring, and a fresh charge of reactants was added.
[d]The product from Ex. 11 was used except a fresh amount of palladium catalyst was added.
[e]Acetylene bubbled through solution continuously.
[f]Bromobenzene used as halide and phenylacetylene as alkyne.
[g]1-chloro-3-nitrobenzene used as halide.

flask was charged with the bromonitrobenzene, the acetylenic charge stock, the catalyst and the amine solvent. The system was then purged with nitrogen for 20 minutes, after which the cuprous iodide was added and the system brought to reaction temperature. Small samples of the reaction mixture were periodically withdrawn by syringe and were subjected to analysis by gas chromatography; and in this manner the reaction was monitored.

Upon termination, the reaction mixture was cooled to room temperature. The reaction solvent was then stripped from the reaction product on a rotary evaporator, followed by the addition of water to the residue to dissolve the salts and any residual amine solvent. Extraction of the aqueous mixture with toluene served to separate the product from the water-soluble components. The organic extract in toluene was then passed through a short column of 200-mesh alumina to remove the palladium catalyst and the cuprous iodide promotor. The toluene was then stripped to provide a crude product. In some cases the product was analyzed at this point by gas liquid chromatography with the aid of mesitylene as an internal standard. In other cases the product was distilled and the distilled product subjected to elemental analysis.

In a first series of runs, 1-bromo-3-nitrobenzene

Referring to Table 1 above, the Conversion ("Conv.") was a weight percent conversion and was calculated by:

$$\frac{\text{Initial wt bromonitrobenzene} - \text{Final wt bromonitrobenzene}}{\text{Initial wt bromonitrobenzene}} \times 100$$

Efficiency ("Eff.") in Table 1 means:

$$\frac{\text{Moles 2-methyl-4-(3-nitrophenyl)-3-butyn-2-ol}}{\text{Initial moles bromonitrobenzene} - \text{Final moles bromonitrobenzene}} \times 100$$

The Yield means the yield of 2-methyl-4-(3-nitrophenyl)-3-butyn-2-ol:

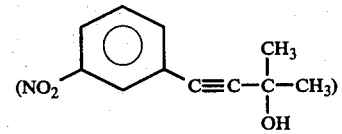

$$(NO_2)-\underset{}{\bigcirc}-C{\equiv}C-\underset{\underset{OH}{|}}{\overset{\overset{CH_3}{|}}{C}}-CH_3)$$

and was calculated as the product of Conversion times Efficiency. Efficiencies and yields were calculated only on isolated crude products by gas chromatography with an appropriate internal standard (mesitylene). In several cases, products of individual runs were not worked up separately but combined in one workup (Exs. 5 to 12). In these cases, conversions were calculated from the gas chromatographs of the gross reaction mixtures without internal standards. The distilled yield of product from combined Exs. 5, 6, 8 and 9 was 83%. This corresponds to an average efficiency of 88%. In Example 1, gas chromatography showed only the presence of a small amount of starting material and the desired product. Due to the small quantities involved, no workup was undertaken.

The time required to reach 50% conversion is a convenient measure of the reaction rate. The data in Table 1 clearly demonstrate that increasing the temperature results in increased reaction rates. Any convenient method for attaining higher temperature can be used. Table 1 demonstrates the use of higher boiling amine solvents. If advantageous for other reasons, low-boiling solvents could be used with elevated pressures to achieve the same result. Increased levels of cuprous iodide promoter also improve the rate (compared Exs. 3 and 4).

As the conversion level approaches 100%, the efficiency to desired product falls slightly as some unidentified heavier materials form. This suggests that optimum yields will be attained in the region of 85–90% conversion.

In Example 7, no reaction was indicated after four hours. It is postulated that the pyridine solvent may have displaced a ligand on the catalyst and deactivated it.

Examples 5 and 9 demonstrate reproducibility.

EXAMPLES OUTSIDE THE SCOPE OF THE INVENTION

EXAMPLE 13

Example 1 was repeated except acetylene was bubbled through the reaction solution continuously in lieu of the bromonitrobenzene. After 6 hours, no reaction was noted by continuous gas liquid chromatographic analysis. The results are summarized in Table 1 above.

Example 13 illustrates that acetylene does not react with bromoarenes. This perhaps is not surprising since the teachings of Sonogashira et al. are specific to the reaction of acetylene with iodoarenes or bromoalkenes.

EXAMPLE 14

Example 1 was repeated except bromobenzene was the halide employed; phenylacetylene was the alkyne; the amount of CuI was increased to 0.25 mmol; and the reaction temperature was increased to 56° C. After 116 hours, the conversion was merely 13%. The results are summarized in Table 1 above.

Example 14, as Example 13, illustrates that phenylacetylene (another specific reactant of Sonogashira et al.) reacts so poorly with bromoarenes that bromoarenes are of no significant interest.

EXAMPLE 15

Example 1 above was repeated except 1-chloro-3-nitrobenzene was employed as the halide. Only traces of the desired

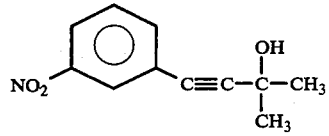

were obtained. Instead a redox reaction occurred in which the 2-methyl-3-butyn-2-ol was oxidized to 2,7-dimethyl-3,5-octadiyn-2,7-diol [(CH$_3$)$_2$C(OH)C≡C—C≡CC(OH) (CH$_3$)$_2$] while the chloronitrobenzene was reduced to 3,3'-dichloroazobenzene (ClC$_6$H$_4$N═NC$_6$H$_4$Cl).

Example 15 illustrates that chloroarenes are not suitable arenes. This, again, is perhaps not surprising since Sonogashira et al. teach that only iodoarenes will react. The results are summarized in Table 1 above.

EXAMPLE 16

Example 1 was repeated except phenylacetylene

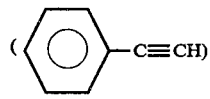

was employed as the sole alkyne (25 mmols); the amount of CuI was increased to 0.25 mmol; and the reaction temperature was increased to 56° C. After 24 hours, the bromonitrobenzene was totally converted, giving an 84% yield of phenyl-3-nitrophenylacetylene

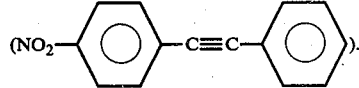

Example 16 shows that it is not predictable (when Ex. 16 is compared with Exs. 13–15) which charge stocks will react with which halogenated arenes.

EXAMPLE 17

(Cleavage Procedure)

A portion (1.4 grams) of the product from Examples 5–12 above [3-methyl-4-(3-nitrophenyl)-3-butyn-2-ol] was dissolved in 15 mls of toluene containing 0.1 gram of powdered NaOH. The mixture was refluxed for one hour. Gas chromatographic analysis revealed that 70% conversion of the charge stock occurred with 90% selectivity to nitrophenylacetylene.

Resort may be had to the variations and modifications as fall within the spirit of the invention and the scope of the appended claims.

We claim:

1. A process for the production of a nitrophenyl hydroxy substituted acetylene which comprises:

reacting a nitrobromobenzene with a substituted terminal acetylene compound containing at least three carbon atoms and an hydroxy group on the carbon atom adjacent to the acetylene group in the presence of a solvent comprising a compound having the formula:

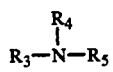

where $R_3$, $R_4$, and $R_5$ can be the same or different and are selected from the group consisting of hydrogen and lower alkyl groups having from 1 to 4 carbon atoms with the proviso that no more than one of said R groups can be hydrogen, and in the added presence of:

a catalyst comprising a compound having the formula:

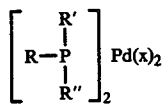

where x can be Br, I, or Cl;

and where R, R' and R" can be the same or different and are selected from the group consisting of phenyl, substituted phenyl and alkyl groups having from 1 to 4 carbon atoms, and a promoter comprising cuprous iodide; to produce HBr and the resultant nitrophenylhydroxyacetylene.

2. A process in accordance with claim 1 wherein the terminal acetylene compound has the formula:

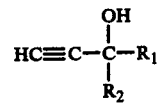

where $R_1$ and $R_2$ can be the same or different and are selected from the group consisting of hydrogen and lower alkyl groups having from 1 to 4 carbon atoms, phenyl and substituted phenyl, and where $R_1$ and $R_2$ can form a saturated 5- or 6-membered ring.

3. A process in accordance with claim 2 wherein $R_1$ and $R_2$ in the terminal acetylene compound are both methyl and wherein the resultant nitrophenylhydroxyacetylene is 2-methyl-4(nitrophenyl)-3-butyn-2-ol.

4. A process in accordance with claim 3 wherein the nitrobromobenzene is meta-nitrobromobenzene and the resultant nitrophenylhydroxyacetylene is 2-methyl-4(3-nitrophenyl)3-butyn-2-ol.

5. A process in accordance with claim 3 wherein the catalyst is bis(triphenylphosphine)palladium dichloride.

6. A process in accordance with claim 5 wherein the solvent is triethylamine.

7. A process in accordance with claim 1 wherein the resultant nitrophenyl hydroxy substituted acetylene compound is converted to nitrophenylacetylene by reacting said nitrophenyl hydroxy substituted acetylene compound with an alkali metal hydroxide in the presence of an aromatic solvent.

8. A process in accordance with claim 7 wherein the alkali metal hydroxide is sodium hydroxide.

9. A process in accordance with claim 8 wherein the aromatic solvent is toluene.

10. A process in accordance with claim 9 wherein said reaction is operated at reflux conditions.

* * * * *